United States Patent
Vadurro et al.

(10) Patent No.: US 6,736,854 B2
(45) Date of Patent: May 18, 2004

(54) PROSTHETIC REPAIR FABRIC WITH EROSION RESISTANT EDGE

(75) Inventors: Valerie Vadurro, Warwick, RI (US);
Roger E. Darois, Foster, RI (US);
Stephen N. Eldridge, Exeter, RI (US);
Michael J. Lee, Barrington, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/143,746

(22) Filed: May 10, 2002

(65) Prior Publication Data

US 2003/0212461 A1 Nov. 13, 2003

(51) Int. Cl.[7] .............. A61F 2/02; A61F 2/04; A61B 17/08
(52) U.S. Cl. .............. 623/23.72; 623/23.64; 606/151
(58) Field of Search .............. 623/23.64, 23.65, 623/23.72, 23.74, 23.76, 23.75, 23.58; 606/151, 154, 153, 215; 600/37

(56) References Cited

U.S. PATENT DOCUMENTS

| | | |
|---|---|---|
| 2,671,444 A | 3/1954 | Pease |
| 3,875,928 A | 4/1975 | Angelchik |
| 4,271,827 A | 6/1981 | Angelchik |
| 4,403,604 A | 9/1983 | Wilkinson et al. |
| 4,769,038 A | 9/1988 | Bendavid et al. |
| 4,796,603 A | 1/1989 | Dahlke et al. |
| 4,854,316 A | 8/1989 | Davis |
| 5,006,106 A | 4/1991 | Angelchik |
| 5,108,420 A * | 4/1992 | Marks .............. 606/213 |
| 5,116,357 A | 5/1992 | Eberbach |
| 5,246,456 A | 9/1993 | Wilkinson |
| 5,258,000 A | 11/1993 | Gianturco |
| 5,290,217 A | 3/1994 | Campos |
| 5,316,543 A | 5/1994 | Eberbach |
| 5,368,602 A | 11/1994 | de la Torre |
| 5,370,650 A | 12/1994 | Tovey et al. |
| 5,397,332 A | 3/1995 | Kammerer et al. |
| 5,433,996 A | 7/1995 | Kranzler et al. |
| 5,456,720 A | 10/1995 | Schultz et al. |
| 5,480,436 A | 1/1996 | Bakker et al. |
| 5,508,036 A | 4/1996 | Bakker et al. |
| 5,593,441 A | 1/1997 | Lichtenstein et al. |
| 5,601,579 A | 2/1997 | Semertzides |
| 5,634,931 A | 6/1997 | Kugel |

(List continued on next page.)

FOREIGN PATENT DOCUMENTS

| | | |
|---|---|---|
| EP | 0 719 527 A1 | 7/1996 |
| EP | 0 898 944 A2 | 3/1999 |

(List continued on next page.)

OTHER PUBLICATIONS

Simpson et al., "Prosthetic Patch Stablization of Crural Repair in Antireflux Surgery in Children," *The American Surgeon*, Jan. 1998, pp. 67–69, vol. 64.

(List continued on next page.)

*Primary Examiner*—Corrine McDermott
*Assistant Examiner*—Alvin Stewart
(74) *Attorney, Agent, or Firm*—Wolf, Greenfield & Sacks, P.C.

(57) ABSTRACT

An implantable prosthesis is provided for repairing or augmenting anatomical weaknesses or defects, and is particularly suitable for the repair of soft tissue and muscle wall openings. The prosthesis may include a layer of fabric that is constructed and arranged to allow tissue ingrowth and is susceptible to erosion into and the formation of adhesions with tissue and organs. The prosthesis is configured to inhibit edge erosion of the prosthesis into surrounding tissue and organs. The prosthesis may include an erosion resistant edge to buffer an edge of the fabric from the adjacent tissue or organs. The erosion resistant edge may be provided along an opening that is adapted to receive a tube-like structure, such as the esophagus.

39 Claims, 7 Drawing Sheets

U.S. PATENT DOCUMENTS

| | | | |
|---|---|---|---|
| 5,695,525 | A | 12/1997 | Mulhauser et al. |
| 5,697,978 | A | 12/1997 | Sgro |
| 5,702,416 | A | 12/1997 | Kieturakis et al. |
| 5,716,409 | A | 2/1998 | Debbas |
| 5,725,577 | A | 3/1998 | Saxon |
| 5,743,917 | A | 4/1998 | Saxon |
| 5,766,188 | A * | 6/1998 | Igaki .......................... 606/151 |
| 5,766,246 | A | 6/1998 | Mulhauser et al. |
| 5,769,864 | A | 6/1998 | Kugel |
| 5,836,961 | A | 11/1998 | Kieturakis et al. |
| 5,916,225 | A | 6/1999 | Kugel |
| 5,919,233 | A | 7/1999 | Knopf et al. |
| 5,948,020 | A | 9/1999 | Yoon et al. |
| 5,954,767 | A | 9/1999 | Pajotin et al. |
| 6,066,777 | A | 5/2000 | Benchetrit |
| 6,067,991 | A | 5/2000 | Forsell |
| 6,090,116 | A | 7/2000 | D'Aversa et al. |
| 6,113,623 | A | 9/2000 | Sgro |
| 6,120,539 | A | 9/2000 | Eldridge et al. |
| 6,174,320 | B1 | 1/2001 | Kugel et al. |
| 6,214,020 | B1 | 4/2001 | Mulhauser et al. |
| 6,224,616 | B1 | 5/2001 | Kugel |
| 6,241,768 | B1 * | 6/2001 | Agarwal et al. ......... 623/11.11 |
| 6,258,124 | B1 | 7/2001 | Darois et al. |
| 6,270,530 | B1 | 8/2001 | Eldridge et al. |
| 6,280,453 | B1 | 8/2001 | Kugel et al. |
| 6,287,316 | B1 | 9/2001 | Agarwal et al. |
| 6,290,708 | B1 | 9/2001 | Kugel et al. |
| 6,319,264 | B1 | 11/2001 | Tormala et al. |
| 6,383,201 | B1 * | 5/2002 | Dong .......................... 606/151 |
| 2001/0049539 | A1 | 12/2001 | Rehil |
| 2002/0001609 | A1 | 1/2002 | Calhoun et al. |
| 2002/0013590 | A1 | 1/2002 | Therin et al. |
| 2002/0042658 | A1 | 4/2002 | Tyagi |
| 2002/0052654 | A1 | 5/2002 | Darois et al. |

FOREIGN PATENT DOCUMENTS

| | | |
|---|---|---|
| EP | 0 898 944 A3 | 8/1999 |
| FR | 2145975 | 2/1973 |
| FR | 2744906 A1 | 8/1997 |
| GB | 1 406 271 | 9/1995 |
| WO | WO 97/35533 | 10/1997 |
| WO | WO 99/56664 | 11/1999 |
| WO | WO 00/07520 A1 | 2/2000 |
| WO | WO 00/42943 | 7/2000 |
| WO | WO 01/08594 A1 | 2/2001 |
| WO | WO 01/54589 A1 | 8/2001 |
| WO | WO 01/81667 A1 | 11/2001 |
| WO | WO 01/85058 A2 | 11/2001 |
| WO | WO 02/22047 A1 | 3/2002 |

OTHER PUBLICATIONS

Paul, et al., "Laparascopic tension–free repair of large paraesophageal hernias", *Surg Endosc.*, 1997, pp. 303–307, vol. 11.

Edelman, David S., M.D., "Laparascopic Paresophageal Hernia Repair with Mesh", *Surgical Laparascopy & Endoscopy*, 1995, pp 32–37, vol. 5, No. 1.

Champion et al., "Laparascopic Mesh Cruroplasty for Large Paraeosphageal Hernias," *Surgical Endoscopy and Other Interventional Techniques*, Feb. 17, 2003, pp. 551–553, vol. 17, No. 4.

Basso et al., "360° Laparoscopic Fundoplication With Tension–Free Hiatoplasty in The Treatment of Symptomatic Gastreoesophageal Reflux Disease," 14 *Surg. Endosc.* 164–169 (2000).

Carlson et al., "Management of Intrathoracic Stomach With Polypropylene Mesh Prosthesis Reinforced Transabdominal Hiatus Hernia Repair," 187(3) *J. Am. Coll. Surg.* 227–230 (1998).

Carlson et al., "Laparoscopic Prosthetic Reinforcement of Hiatal Herniorrhaphy," 16 *Dig. Surg.* 407–410 (1999).

Carlson et al., "Polypropylene Mesh Reinforced Hiatus Hernia Repair," 112(4) *Gastroentology* (Apr. 1997).

Carugno et al., "Development of an Adjustable Prosthesis For The Treatment of Gastroesophageal Reflux," 44 *ASAIO Journal* 140–143 (1998).

Frantzides et al., "Laparoscopic Repair of Large Hiatal Hernia With Polytetrafluoroethylene," 13 *Surg. Endosc.* 906–908 (1999).

Frantzides et al., "Prosthetic Reinforcement of Posterior Cruroplasty During Laparoscopic Hiatal Herniorrhaphy," 11 *Surg. Endosc.* 769–771 (1997).

Huntington, "The Surgeon at Work: Laparoscopic Mesh Repair of The Esophageal Hiatus," 184 *J. Am. Coll. Surg.* 399–400 (Apr. 1997).

Kennedy, "Hiatus Hernia Repair Clinical and Radiological Results of a New Combined Thoracoabdominal Technique," 1 *Med. J. Australia* 386–390 (1974).

Kozarek et al., "Evaluation of Angelchik Antireflux Prosthesis: Long Term Results", 30(8) *Digestive Diseases and Sciences* 723–732 (Aug. 1985).

Lees et al., "Esophageal Perforation: A Complication of The Angelchik Prosthesis," 50(4) *Cleve. Clin. Q.* 449–451 (1983).

Patel et al., "Angelchik Antireflux Prosthesis—Its Usefulness And Review of Literature," 79(1) *Am. J. of Gastroenterology* 12–15 (1984).

Sakashita et al., "Repair of Posttraumatic and Recurrent Diaphragm Hernias With Prosthetic Mesh," 15(1) *Acta Medica et Biologica* 1–14 (1967).

Thibault et al., "The Angelchik Antireflux Prosthesis: Long-Term Clinical and Technical Follow–Up," 37(1) *Canadian J. Surg.* 12–17 (Feb. 1994).

Waldhausen et al., "The Diagnosis and Management of Traumatic Injuries of the Diaphragm Including The Use of Marlex Prostheses," 6(3) *J. of Trauma* 332–343 (1966).

Watanabe et al., "Laparoscopic Repair of a Paraesophageal Hiatus Hernia Without Fundoplication," 27 *Surgery Today* 1093–1096 (1997).

* cited by examiner

PROSTHETIC REPAIR FABRIC WITH EROSION RESISTANT EDGE

FIELD OF THE INVENTION

The present invention relates to an implantable prosthesis, and more particularly to a prosthetic repair fabric for use in soft tissue repair and reconstruction.

DISCUSSION OF RELATED ART

Various prosthetic repair materials have been proposed to repair and reinforce anatomical defects, such as tissue and muscle wall hernias. For example, a hiatal hernia occurs when a natural opening, or "hiatus," in the diaphragm through which the esophagus extends, becomes enlarged, allowing the stomach to pass through the hiatus into the thoracic cavity.

Representative surgical treatments for a hiatal hernia may include a cruroplasty, which involves tightening the crura of the diaphragm around the esophagus to reduce the size of the hiatal hernia. It has also been known to use a prosthetic repair fabric in the surgical treatment of a hiatal hernia. Typically, a sheet of surgical mesh fabric, such as BARD MESH, commercially available in rectangular stock sheets, was custom fashioned by a surgeon into a shape suitable for a particular patient's hiatal repair, such as a rectangular or oval shape. Typically, the surgeon placed the mesh implant over the hiatal hernia and proximate to the esophagus.

It is one object of certain embodiments of the present invention to provide a prosthesis for the treatment of tissue or muscle wall defects, including hiatal hernias.

It is another object of certain embodiments of the present invention to provide a prosthesis for the repair of tissue defects, such as hiatal hernias, that reduces the incidence of postoperative erosion to tissue and organs, such as the esophagus, stomach and/or other surrounding viscera.

SUMMARY OF THE INVENTION

In one illustrative embodiment of the invention, a prosthetic repair fabric is provided for repairing a tissue or muscle wall defect. The prosthetic repair fabric comprises a layer of fabric that is susceptible to erosion into and the formation of adhesions with tissue and organs, and an edge barrier that inhibits erosion into tissue and organs and inhibits the formation of adhesions with tissue and organs. The layer of fabric includes first and second surfaces and a fabric edge extending from the first surface to the second surface. The first surface is adapted to face the tissue or muscle wall defect and the second surface is adapted to face away from the defect. The edge barrier is disposed on a portion of the first and second surfaces adjacent the fabric edge and extends from the first surface to the second surface over the fabric edge. The edge barrier has an inner surface that is spaced from the fabric edge in a direction normal to the fabric edge to form a gap between the inner face of the edge barrier and the fabric edge to inhibit erosion of the tissue and organs by the fabric edge and to inhibit the formation of adhesions to the fabric edge.

In another illustrative embodiment of the invention, a prosthetic repair fabric is provided for repairing a tissue or muscle wall defect. The prosthetic repair fabric comprises a layer of fabric that is susceptible to the formation of adhesions with and erosion into tissue and organs, and an edge barrier that inhibits erosion into tissue and organs and inhibits the formation of adhesions. The layer of fabric includes first and second surfaces and a fabric edge extending from the first surface to the second surface. The first surface is adapted to face the muscle or tissue wall defect and the second surface is adapted to face away from the defect. The edge barrier is disposed at all times over the fabric edge. The edge barrier has an inner surface that is spaced from the fabric edge in a direction normal to fabric edge to form a gap between the inner face of the edge barrier and the fabric edge to inhibit erosion of the tissue and organs by the fabric edge and to inhibit the formation of adhesions to the fabric edge.

In one illustrative embodiment of the invention, a prosthetic repair fabric is provided for repairing a tissue or muscle wall defect. The prosthetic repair fabric comprises a body of implantable, biocompatible repair fabric. The body includes first and second surfaces and a body edge that extends from the first surface to the second surface. The body also includes first and second layers joined to each other along an inverted seam that extends inwardly from the body edge and between the first and second layers to inhibit erosion of the tissue and organs.

In a further illustrative embodiment of the invention, a prosthetic repair fabric is provided for repairing a tissue or muscle wall defect. The prosthetic repair fabric comprises a body of implantable, biocompatible repair fabric. The body includes first and second surfaces and a body edge extending from the first surface to the second surface. The first surface is adapted to face the muscle or tissue wall defect and the second surface is adapted to face away from the defect. The body includes first and second layers, each of the first and second layers having an outer surface and an inner surface. The outer surface of the first layer forms the first surface of the body and the outer surface of the second layer forms the second surface of the body with the inner surface of the first layer facing the inner surface of the second layer. The first and second layers are joined to each other along at least one seam that is disposed inwardly of the body edge between the inner surfaces of the first and second layers to inhibit erosion of the tissue and organs by the body edge.

In another illustrative embodiment of the invention, a method is provided for fabricating a prosthetic repair fabric for repairing a tissue or muscle wall defect. The method comprises joining an outer edge of a first layer of implantable, biologically compatible material to an outer edge of a second layer of implantable, biologically compatible material. Each of the first and second layers includes first and second surfaces. The first and second layers are joined to each other with the first surface of the first layer facing the second surface of the second layer. After joining the first and second layers, the method further comprises inverting the first and second layers so that the second surface of the first layer is facing the first surface of the second layer and the outer edges of the first and second layers extend inwardly between the second surface of the first layer and the first surface of the second layer, thereby isolating the outer edges of the first and second layers from tissue and organs so as to inhibit erosion into the tissue and organs when the prosthetic repair fabric is implanted to repair the tissue or muscle wall defect.

Other objects and features of the present invention will become apparent from the following detailed description when taken in connection with the accompanying drawings. It is to be understood that the drawings are designed for the purpose of illustration only and are not intended as a definition of the limits of the invention.

BRIEF DESCRIPTION OF THE DRAWINGS

The foregoing and other objects and advantages of the invention will be appreciated more fully from the following drawings, wherein like reference characters designate like features, in which.

DESCRIPTION OF ILLUSTRATIVE EMBODIMENTS

Figure 1:
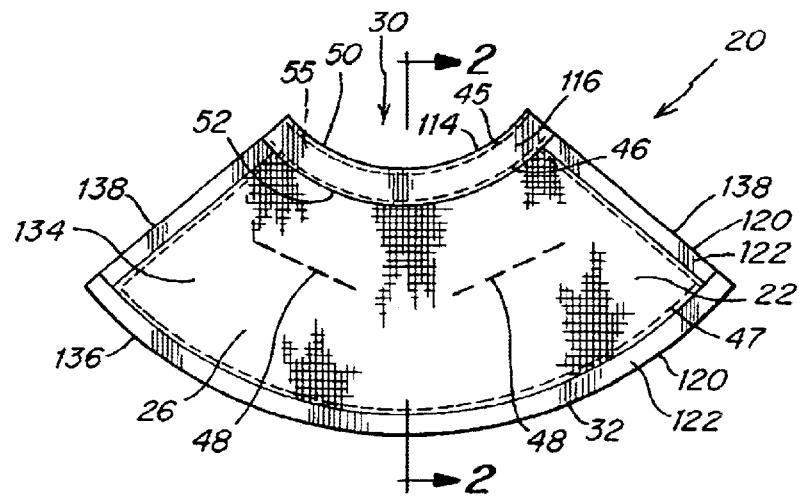
FIG. 1 is a top plan view of a prosthetic repair fabric in accordance with one illustrative embodiment of the present invention.

The invention is directed to an implantable prosthesis for repairing or augmenting anatomical weaknesses or defects, and is particularly suitable for the repair of soft tissue and muscle wall openings. For ease of understanding, and without limiting the scope of the invention, the prosthesis to which this patent is addressed is described below particularly in connection with a hiatal hernia repair. It should be understood, however, that the prosthesis is not so limited and may be employed in other anatomical procedures, as would be apparent to one of skill in the art. For example, the prosthesis may be used where a tube-like structure, including a spermatic cord or other projection, extends from or passes through an opening in a tissue muscle or organ wall requiring repair and/or augmentation.

The invention is more particularly directed to a prosthesis that is configured to reduce the incidence of post-operative erosion into adjacent tissue or organs, such as the esophagus or other cord-like structure, that may come into contact with the prosthesis. Tissue and organs may be particularly susceptible to erosion or abrasion by the edge of a prosthetic repair fabric that is positioned proximate to tissue and organs which lie transverse to the plane of the prosthetic fabric material, particularly in dynamic environments, such as the diaphragm. Thus, the prosthesis may be provided with one or more erosion-resistant edges that act to buffer or otherwise isolate the edge of the repair fabric so as to reduce the incidence of erosion into adjacent tissue or organs.

A prosthesis with erosion resistant characteristics may be particularly suitable in the repair of a hiatal hernia. The esophagus presents a projecting structure proximate and generally perpendicular to the plane of the defect in the diaphragm. The diaphragm moves to assist in breathing with sudden and extreme movement occurring in the case of coughing or sneezing, while the esophagus moves to assist in swallowing and regurgitating. This very dynamic environment of the esophagus and diaphragm may increase potential erosion of the esophagus by a prosthesis implanted to repair the defect.

Erosion into adjacent tissues and organs may be affected by various factors and characteristics of the prosthetic repair fabric. For example, a more deformable prosthetic material may be less likely to erode into adjacent tissue and organs than a stiffer material. Similarly, a smoother or less abrasive material may be desirable to reduce erosion. The surface area of an edge presented to adjacent tissue and organs may be another factor, such that a broader edge may help distribute forces over a larger surface area to reduce erosion of tissue and organs. The edge of the repair fabric may be provided with a degree of resiliency or spring-like action that creates a cushion or bumper effect between the repair fabric and adjacent tissue and organs. Thus, the prosthesis may be configured with any one or combination of two or more of these or other characteristics or features as would be apparent to one of skill in the art to reduce or inhibit erosion of tissue or organs.

In some situations, adhesions to the implant may be undesirable since the prosthesis may work its way deep into or even through the tissue and/or the tissue may adhere to the prosthesis and be repetitively torn away with body and muscle movements. Such adhesions and/or resulting scar tissue around the circumference of a cord-like structure, such as the esophagus, spermatic cord or other projection, may lead to strangulation of the structure.

While embodiments discussed below include an implant having one or more portions that are tissue infiltratable, the invention is not so limited and also contemplates a prosthesis that is not arranged for tissue ingrowth. Still further embodiments include implants where tissue infiltratable or otherwise erosion and/or adhesion sensitive portions are rendered resistant to erosion and/or adhesion formation. In certain embodiments, some or all portions of the implant may be arranged for tissue ingrowth, while in other embodiments some or all portions of the implant may be arranged to resist tissue ingrowth or otherwise to resist erosion and/or the formation of adhesions to and strangulation of neighboring tissue and organs. The location of tissue ingrowth sections and barrier sections may vary along an edge of the implant, a surface of the implant, and/or sections of a body portion of the implant, as discussed below.

An implant according to the present invention, in connection with a hiatal repair, may include a body portion constructed and arranged to cover the enlarged or weakened portion of the hiatus, or the operative sutures used in repairing the hernia, such as are placed in a cruroplasty. Some or all of the body portion may be tissue infiltratable, may be impervious to tissue ingrowth or otherwise resistant to erosion, or may include a combination of tissue infiltratable and erosion resistant regions. In some embodiments, the prosthesis may be arranged to reduce the incidence of erosion and/or the formation of post-operative adhesions, or strangulation of the cord structure. The implant may be formed of a single or of multiple layers of prosthetic repair material, and the number of layers of prosthetic material may vary in different portions of the implant.

The implant may have a complete or partial opening that is adapted to receive the esophagus or other cord-like structure. The opening may be formed along any one, or a combination, of the sides of the implant or may be provided within and through the body portion. For the purposes of this patent specification, as well as any claims related thereto, the feature of an "opening" adapted to receive the esophagus or tube-like structure shall include a complete opening that is configured to completely surround the esophagus, and a partial opening that is configured to only partially surround the esophagus, even though the qualifier of "complete" or "partial" is not used. The opening may have a round shape or any other shape that is constructed and arranged to position the implant about the esophagus. A slit may also be formed extending from the opening to the periphery of the prosthesis to provide an access opening for the esophagus.

The implant may be defined by an anterior end, a posterior end, a medial side and a lateral side. The sides and ends may be of the same or of differing length and/or shape. Any of the sides and ends may include a single straight edge, a curved edge, an edge formed of diverging or converging segments, and other shapes as would be apparent to one of skill in the art. The implant, viewed end-to-end or side-to-side may be symmetrically shaped or asymmetrically shaped. The implant may have a circular shape, an ovoid or an egg shape, a C-shape, a bow tie shape, a butterfly shape, a rectangular shape, an arc shape, and other shapes as would be apparent to one of skill in the art.

The implant may be elongated in the anterior-posterior direction, in the medial-lateral direction or in a combination of the anterior-posterior and medial-lateral directions. An implant having substantially the same length in all directions also is contemplated. The implant may be preshaped or may be custom shaped by the surgeon prior to or during the surgical procedure. Similarly, the implant may be prearranged with the slit and keyhole opening, or one or both of these features may be left to the surgeon to form.

The implant may, in an unstressed or natural state, such as prior to implantation, have a generally flat or planar shape, or may be arranged with a concave and/or convex shape on one or more surfaces, or may include a more complex three dimensional shape. A cord or other member may be threaded through the implant and then manipulated, such as by drawing ends of the cord extending outside of the implant, to transform the prosthesis into a desired shape. The implant may be provided with shape influencing members, such as thin strips of metal, polymer, and the like, that may be engaged to, or otherwise in contact with, the implant and naturally or upon application of a force (e.g., heat) cause the prosthesis to form a predetermined shape.

The implant may be sufficiently flexible to allow a surgeon to manipulate the fabric to conform to the surgical site and ease delivery during a laparoscopic procedure, or may have a stiffer arrangement that limits compression and/or expansion of the repair device. In certain embodiments, the implant may be collapsible, such as by folding, rolling, or otherwise, into a slender configuration that may be delivered through a narrow lumen of a laparoscopic cannula or trocar. The flexibility of the implant is influenced by many factors including the materials from which the implant is constructed, any shape influencing members, treatments applied to the material of the implant, and the amount of stitching or other attachment features in the body of the implant.

Certain portions of the implant may include a barrier which may be formed, for example and without limiting the invention, by applying a barrier material to selective regions of the prosthesis, by rendering selected porous regions of the implant less porous and, preferably, impervious to tissue infiltration, and by other arrangements as would be apparent to one of skill in the art. The barrier may be arranged to isolate the esophagus, and/or the abdominal viscera, from selected portions of the implant that are abrasive or tissue infiltratable, reducing the incidence of esophageal, stomach, liver, and intestine trauma associated with erosion, adhesion, constriction and the like.

As an example, and without limiting the inventive arrangements contemplated for isolating the esophagus and viscera from various potential points of erosion and/or adhesion to the implant, the opening edge may be arranged with an opening edge barrier so that the opening edge is isolated from the portion of the esophagus passing through the opening. The margin areas surrounding the opening on the first, or diaphragm facing, surface of the implant also may be isolated by an edge barrier, limiting the prospects of contact between the segment of the esophagus extending through and adjacent the opening and the margins of the opening. Some or all of the second surface of the prosthesis, that is the surface which will face the viscera, may include a surface barrier. The surface barrier may be arranged to cover substantially the entire second surface. A further outer edge barrier may be arranged at the outer edge of the prosthesis to prevent adhesions with the cavity viscera by the outer periphery of the prosthesis. The outer edge barrier may also be configured or extended to isolate the margin of the first surface extending adjacent the outer edge of the layer of fabric. The keyhole slit, if provided, may also have a slit barrier portion. The slit edges and/or the margin adjacent the slit edges of the tissue infiltratable fabric at the keyhole slit may also encompass a slit barrier. The shape and dimension of the various barrier portions may be modified as would be apparent to one of skill in the art, and the invention is not limited to the particular configuration of the barrier sections illustrated in the figures.

FIGS. 1–4 illustrate one embodiment of a prosthetic repair fabric for repairing soft tissue and muscle wall defects, particularly defects located proximate a tube-like structure, such as the esophagus, spermatic cord or other projection, extending from or passing through an opening in a tissue, muscle or organ wall. The prosthetic repair fabric may be configured to promote enhanced tissue ingrowth while limiting the incidence of post-operative erosion into the surrounding tissue and organs. The prosthesis 20 includes a body portion 134 that is configured to cover the enlarged or weakened portion of the defect or the operative sutures repairing the defect. The body portion has a first surface 26 for facing the defect region, such as the diaphragm, and a second surface 28 for facing the viscera. The body portion may include a tissue infiltratable fabric 22. One or more regions of the body portion may be configured as erosion resistant to limit the incidence of postoperative erosion of selected regions of the fabric into adjacent tissue and organs, such as the esophagus or other cord-like structure.

The prosthesis may be rendered erosion resistant by applying a barrier material to one or more selective regions of the implant, by rendering selective abrasive regions of the implant less abrasive, and by other arrangements as would be apparent to one of skill in the art. For example, an erosion resistant region may be smoother, softer, broader, and/or more deformable than other portions of the implant. The prosthesis may include an erosion resistant barrier arranged to isolate the esophagus and/or abdominal viscera from selected portions of the implant.

The erosion resistant barrier and/or additional barrier regions of the prosthesis may be rendered adhesion resistant to limit the incidence of postoperative tissue adhesion between the prosthesis and adjacent tissue, muscle, and/or organs. Accordingly, the prosthesis may also include one or more barriers that are configured and arranged to isolate the tissue infiltratable fabric so as to inhibit undesirable adhesions.

For example, and without limiting the inventive arrangements contemplated for isolating the fabric from various points of adhesion and erosion, the prosthesis may include any one or combination of a surface barrier on one or both sides of the fabric, an edge barrier along one or more edges of the fabric, and/or a margin barrier located proximate to one or more edges of the fabric. The shapes, sizes and locations of the various barriers may be selected to achieve any desired adhesion and/or erosion resistant characteristics for the prosthesis as would be apparent to one of skill in the art.

The adhesion resistant regions may be formed, for example and without limiting the invention, by applying a barrier material to selective regions of the prosthesis, by rendering selective porous regions of the implant less porous and, preferably, impervious to tissue infiltration, and by other arrangements as would be apparent to one of skill in the art. The adhesion resistant barrier may be arranged to isolate the esophagus and/or the abdominal viscera from selected portions of the implant that are tissue infiltratable, reducing the incidence of post operative tissue adhesions.

The erosion resistant and adhesion resistant barriers are each directed to improving particular disadvantages in the prior art. However, actual materials and/or barrier configurations which may be used to reduce erosion into surrounding tissue and organs may also have adhesion resistant characteristics, such as limited porosity for resistance to tissue infiltration. Thus, any barrier region may be erosion resistant, adhesion resistant, or both erosion and adhesion resistant.

In the illustrative embodiment shown in FIGS. 1–4, the prosthesis includes an erosion resistant edge barrier 114 that is configured to isolate and buffer an edge 54 of the fabric 22 from adjacent tissue or organs, such as the esophagus.

The edge barrier 114 extends from the first surface 26 of the body portion, over the fabric edge 54, and then back toward the second surface 28 of the body. In this manner, the fabric edge 54, which extends between the first and second surfaces of the fabric, is covered by the erosion resistant edge barrier 114 so that the portion of the esophagus passing adjacent the edge is isolated from and does not directly contact the fabric edge.

As shown, portions of the barrier 114 may extend beyond the fabric edge to form a first extension 700 and second extension 702 that project beyond the edge of the fabric. In one embodiment, the barrier 114 is formed from a material that is more deformable than the fabric edge so that the barrier 114 may deform or move relative to the fabric edge to buffer the esophagus from abrasions by the edge of the fabric.

In the illustrative embodiment, the erosion resistant edge barrier 114 includes an inner surface 502 that is spaced from the fabric edge 54 by a distance D in a direction that is approximately normal to the fabric edge. This arrangement forms a gap or pocket 500 between the inner surface of the edge barrier and the fabric edge. The pocket 500 forms a cushion space that provides a bumper effect or spring-like action to pillow or otherwise cushion the esophagus from the implant.

Figure 3:
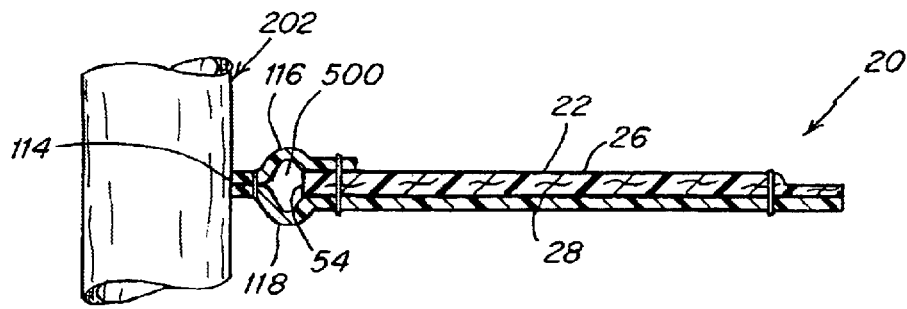
FIG. 3 is a schematic view of the prosthetic repair fabric of FIG. 1 implanted in the abdominal cavity proximate to the esophagus.
Figure 4:
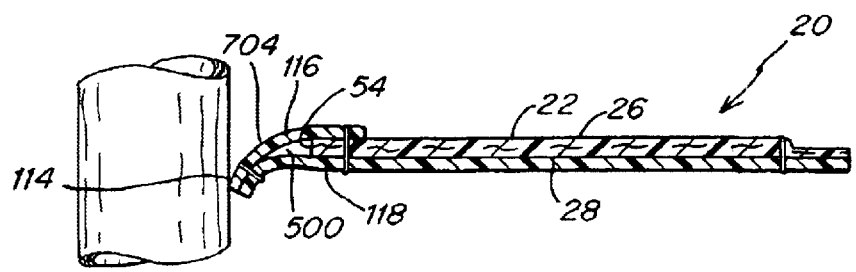
FIG. 4 is another schematic view of the prosthetic repair fabric of FIG. 1 implanted in the abdominal cavity proximate to the esophagus.

FIGS. 3–4 schematically illustrate several examples of the cushioning effect of the erosion resistant edge 114 of the prosthesis when engaged by adjacent tissue or organs. It is to be appreciated, however, that the prosthesis may employ any suitable arrangement for providing an erosion resistant edge.

As shown in FIG. 3, the edge barrier 114 and the pocket 500 may compress toward the fabric edge to cushion or bumper the esophagus 202 in response to a force F between the esophagus and the implant in a direction generally perpendicular to the fabric edge 54. In this manner, the first and second extensions 700, 702 of the edge barrier may also bow away from each other to present a larger surface area to the esophagus to enhance force distribution between the edge and the esophagus for added erosion resistance.

Rather than being compressed, the edge barrier 114 may bend relative to the fabric edge, as shown in FIG. 4, when engaged by the esophagus 202. In this manner, the edge barrier forms a ledge 704 having a broad surface area, as compared to the fabric edge, that may distribute abrasive forces between the implant and the esophagus over a larger surface area to reduce potential erosion. The construction or material of the edge barrier 114 may also provide a resilient or spring-like action, such that the ledge may buffer and cushion the esophagus from the fabric edge 54 and then return to an essentially planar position when not engaged by the esophagus.

As is to be appreciated, it may be desirable to configure the edge barrier 114 so as to bend and flex relative to the fabric edge in a manner that provides a desired amount of erosion resistance. Various factors may effect the particular configuration of the edge barrier, including the stiffness of the fabric, the stiffness of the barrier material, the resiliency of the barrier material, and the weight of the barrier material. For example, the distance between the inner surface of the edge barrier 114 and the fabric edge 54 may be as large as 3.0 mm. In one embodiment, for a repair fabric formed of polypropylene mesh and an edge barrier formed of ePTFE, the distance ranges from approximately 1.0 mm to approximately 2.5 mm. In another embodiment, for a repair fabric made of PTFE mesh which is more flexible than polypropylene, the distance is less than approximately 1.5 mm. Of course, the spacing between the inner surface of the edge barrier and the fabric edge may vary as would be apparent to one of skill in the art to provide any desirable level of erosion resistance.

In certain repairs located proximate a tube-like structure, such as the esophagus, an edge of the prosthesis may be configured to accommodate or conform to the esophagus or other like structure. In the illustrative embodiment of FIGS. 1–4, the prosthesis is provided with an opening 30 that is adapted to receive the esophagus. The opening 30 is located along an edge of the body portion of the prosthesis so that the esophagus is only partially surrounded by the prosthesis when it is implanted at the defect site. It is to be appreciated that the opening may be provided on any suitable portion of the prosthesis for a particular repair. For example, the opening may be located along one or more sides of the prosthesis or within the body portion so that the esophagus is completely surrounded by the prosthesis. The opening may have a curved or rounded shape or any other shape that is adapted to conform to the esophagus. For a complete opening which is configured to completely surround the esophagus, a slit may be formed from the opening to the periphery of the prosthesis to provide an access passage for the esophagus.

In the illustrative embodiment of FIGS. 1–4, the erosion resistant edge barrier 114 is provided along the edge of the opening 30 to isolate and buffer the esophagus from the opening edge. It is to be appreciated, however, that the erosion resistant edge barrier may be provided along one or more other edges of the prosthesis as would be apparent to one of skill in the art.

As indicated above, one or more selected regions of the prosthesis 20 may also be rendered adhesion resistant to limit the incidence of postoperative tissue adhesion between the prosthesis and adjacent tissue, muscle and/organs, such as the esophagus, spleen, liver, stomach, bowel, small and large intestine in the abdominal cavity or the heart and lungs in the thoracic cavity. In this regard, the prosthesis may include one or more barriers that are configured and arranged to isolate the tissue infiltratable fabric so as to inhibit undesirable adhesions. For example, the prosthesis may include any one or a combination of two or more of a surface barrier on one or both sides of the fabric, an edge barrier along one or more edges of the fabric and/or a margin barrier located proximate to one or more edges of the fabric. The shapes, sizes and locations of the various barriers may be selected to achieve any desired adhesion resistant characteristics for the prosthesis as would be apparent to one of skill in the art.

In the illustrative embodiment shown in FIGS. 1–4, the prosthesis includes a surface barrier 118 that is arranged to cover substantially the entire second surface 28 (viscera facing surface) of the fabric 22. In this manner, the surface barrier inhibits the formation of adhesions between the fabric and the cavity viscera located opposite the defect site. In one embodiment, the surface barrier 118 includes a sheet of adhesion resistant material that is attached to the fabric.

The prosthesis also includes an opening margin barrier 116 to isolate the esophagus from portions of the fabric 22 proximate the opening 30. More particularly, the opening edge 54 is covered by the opening edge barrier 114 so that the portion of the esophagus passing through the opening does not directly contact the opening edge of the fabric. Similarly, a marginal portion 55 of the first surface 26 (diaphragm facing) surrounding the fabric opening is isolated by the opening margin barrier 116. The margin barrier limits the prospect of adhesions between the segment of the esophagus extending through and adjacent the opening and the marginal portions of the fabric proximate the opening.

In the illustrative embodiment, the opening margin barrier 116 includes a partial annular ring of barrier material that overlies the first surface 26 of the fabric 22 at the marginal portion 55 surrounding the opening 30. As shown, the first extension 700 of the margin barrier extends beyond the opening edge 54 of the fabric. Similarly, the second extension 702 of the surface barrier 118 extends beyond the opening edge of the fabric so as to lie adjacent the margin barrier. The margin barrier 116 is attached directly to the surface barrier 118, without the intervening layer of fabric therebetween, to form the erosion resistant edge barrier 114 which isolates and buffers the opening edge of the fabric from the esophagus. The attachment at the outer edge of the margin barrier 116 and the surface barrier 118 forms the inner surface 502 of the edge barrier that is spaced from the edge 54 of the fabric by the pocket 500. As is to be appreciated, this configuration also renders the edge barrier 114 adhesion resistant.

The prosthesis further includes an outer edge barrier 120 that extends around at least a portion of the outer peripheral edge to reduce the incidence of adhesions between the cavity viscera and the outer periphery 32 of the prosthesis. In the illustrative embodiment, the outer edge barrier extends about the edge of the periphery of the prosthesis other than the opening edge. The outer edge barrier 120 is formed by rendering a peripheral segment of the fabric 22 adhesion resistant. In one embodiment, the outer edge barrier is formed by melting and resolidifying or otherwise heat sealing the outer periphery of the fabric. It is to be understood, however, that the outer edge barrier may be formed by any suitable arrangement apparent to one of skill in the art. For example, a barrier material may be used to cover the fabric periphery or otherwise render the fabric adhesion resistant along the periphery. Examples of suitable outer edge barriers are described in U.S. application Ser. No. 09/661,623, assigned to C. R. Bard, which is incorporated herein by reference.

An outer margin barrier is also provided to isolate a marginal portion of the fabric proximate the outer peripheral edge of the prosthesis. The outer margin barrier 122 extends inwardly from the outer edge along the first surface 26 of the fabric layer 22 to limit the likelihood of adhesion formation to the prosthesis were the outer edge 32 to fold back during placement or otherwise be exposed to tissue and organs post procedure. In one embodiment, the outer margin barrier is formed by melting and resolidifying the outer marginal portion of the fabric. However, any suitable isolation arrangement may be employed as would be apparent to one of skill, including the various barrier arrangements described above.

Figure 2:
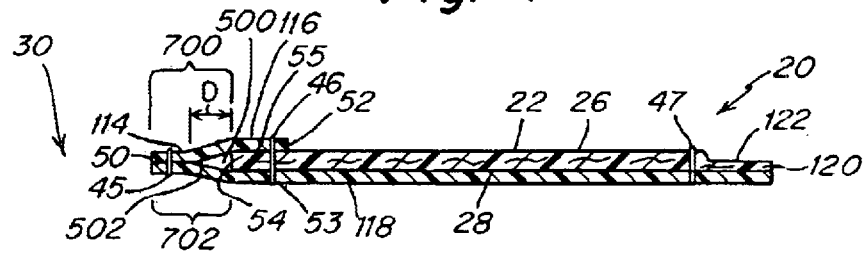
FIG. 2 is a cross-sectional view of the prosthetic repair fabric of FIG. 1 taken along section line 2—2.

In the illustrative embodiment shown in FIGS. 1–4, the erosion resistant edge barrier 114, the opening margin barrier 116 and the surface barrier 118 are stitched to the fabric 22 with a series of continuous connecting stitches. As shown in FIGS. 1–2, a pair of stitch lines 45, 46 attach the annular barrier layer 116 and a portion of the surface barrier 118 to the fabric 22 to form the erosion resistant edge barrier 114. The first line of stitches 45 attaches the extension portions 700, 702 of the barrier layers 116, 118 directly to each other to form the opening edge barrier 114 which isolates and buffers the opening edge 54 of the fabric 22 from the esophagus. The second line of stitches 46 attaches the inner circumference 52 of the opening margin barrier 116 and corresponding region 53 of the surface barrier 118 to the fabric 22. A third stitch line 47 attaches the outer perimeter of the surface barrier 118 to the fabric along the outer periphery 32 of the implant.

It may be desirable to provide the surface barrier 118 with some amount of slack so that the barrier does not necessarily lie directly against the second surface of the fabric 22. In this manner, the surface barrier is not tautly drawn against the surface of the fabric, thereby allowing slight billowing of the barrier, which may enhance the tissue integrability of the prosthesis. In one embodiment, the portion of the surface barrier 118 extending between the second and third stitch lines 46, 47 is configured to billow slightly relative to the fabric.

In some arrangements, it may be desirable to control, if not essentially eliminate, the amount of billowing between the surface barrier 118 and the fabric layer 22. As shown in the illustrative embodiment of FIGS. 1–2, the separation between the surface barrier 118 and the layer of fabric 22 may be controlled with intermittent attachment points 48 located, as desired, between the second and third stitch lines 46, 47. The number and location of the intermittent attachment points, if even desired, may be selected to achieve any desired billowing characteristic as would be apparent to one of skill in the art.

It is to be understood that other suitable stitch patterns may be implemented for connecting one or more of the barriers to the fabric 22. Examples of other stitch patterns include, but are not limited to, a plurality of intermittent stitches between the barrier and the fabric, or a single line of continuous stitches that follow the contour of the periphery 32 and form a concentric, spiral pattern from the outer periphery 32 to the middle of the body of the prosthesis. It may be desirable in certain cases to limit the amount and/or location of stitching to avoid sealed pockets within the prosthesis. Intermittent stitches or gaps in continuous stitches may encourage fluid flow into and out of volumes delimited by the layers of fabric and/or barrier materials. It also may be desirable to limit the amount of stitching to maintain the flexibility of the prosthesis. Appropriate biocompatible thread materials may be used for joining the barrier and tissue infiltratable materials together, as would be apparent to one of skill in the art. For example, the stitches may include, but are not limited to, polypropylene monofilament or ePTFE yarn.

Rather than stitching the barrier materials to the fabric, other attachment methods may be employed as would be apparent to one of skill in the art. For example, the barrier and the fabric may be attached using any suitable tacking, stapling, heat bonding, chemical bonding and molding techniques.

Figure 5:
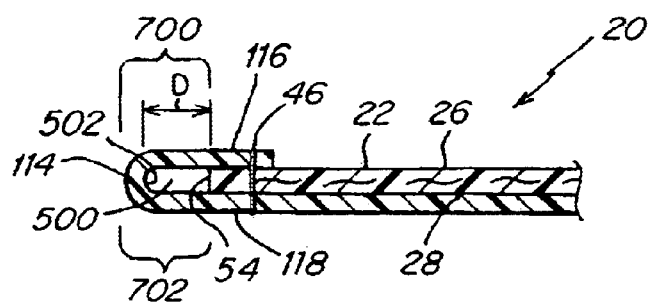
FIG. 5 is a fragmented, cross-sectional view, similar to FIG. 2, of an edge barrier of a prosthetic repair fabric in accordance with another illustrative embodiment of the present invention.
Figure 6:
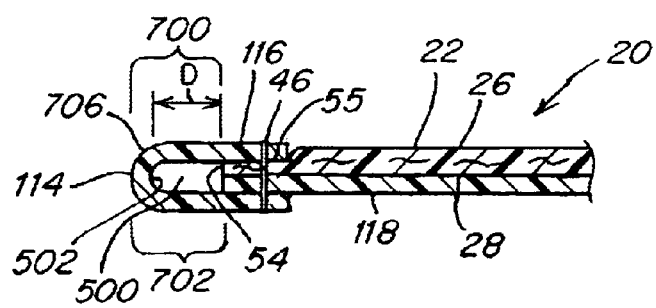
FIG. 6 is a fragmented, cross-sectional view, similar to FIG. 2, of an edge barrier of a prosthetic repair fabric in accordance with a further illustrative embodiment of the present invention.
Figure 7:
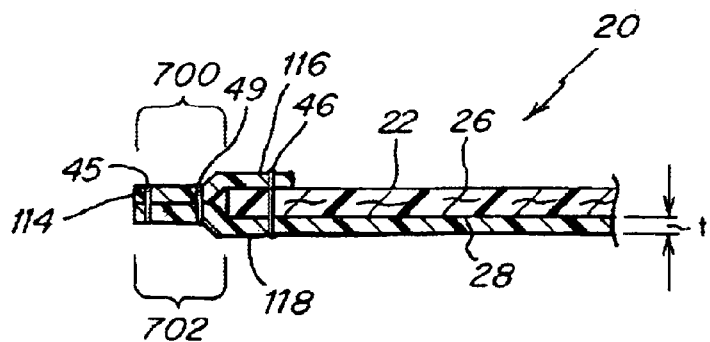
FIG. 7 is a fragmented, cross-sectional view, similar to FIG. 2, of an edge barrier of a prosthetic repair fabric in accordance with another illustrative embodiment of the present invention.
Figure 8:
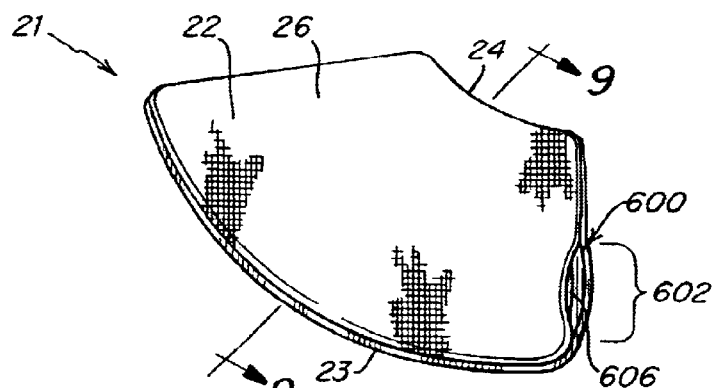
FIG. 8 is a perspective view of a prosthetic repair fabric in accordance with another illustrative embodiment of the present invention.

The prosthesis 20 may employ an erosion resistant edge formed using any suitable arrangement apparent to one of skill in the art. Examples of other illustrative embodiments of an erosion resistant edge are shown in FIGS. 5–7. It is to be understood that each of these embodiments may also render the edge-adhesion resistant.

In the illustrative embodiment shown in FIG. 5, the erosion resistant edge barrier 114 extends from the surface barrier 118 on the second surface 28 (viscera facing surface) of the fabric 22 and across the opening edge 54 of the fabric. The barrier material wraps about the opening edge 54 and onto the first surface of the fabric 22 to form the opening margin barrier 116. As shown, the barrier material is loosely wrapped or draped about the opening edge 54 of the fabric to form a gap 500 between the inner surface 502 of the edge barrier and the fabric edge 54 that acts to buffer or cushion the esophagus or other cord-like structure from the fabric edge.

Wrapping the barrier material about the opening edge of the fabric layer provides a continuous, integrated structure for the surface barrier 118, the erosion resistant edge barrier 114, and the opening margin barrier 116. In addition, loosely folding the barrier material over a non-linear or curved edge may reduce the formation of stiff pleats and folds in the barrier material. Limiting stiff pleats and folds may be desirable to reduce erosion that may potentially occur with stiff points or edges in the barrier material.

In the illustrative embodiment shown in FIG. 6, the erosion resistant edge barrier 114 includes a separate, continuous barrier cuff 706 that is loosely wrapped about the opening edge 54 of the fabric. In this regard, the cuff extends continuously from the opening margin 55 on the first surface of the fabric, across the opening edge 54, and onto a portion of the surface barrier 118 adjacent the opening edge. Thus, the cuff is configured to provide the margin barrier 116 on the first surface of the fabric, and the erosion resistant edge barrier 114 for isolating and buffering the opening edge. Similar to the embodiments described above, the loose wrapping of the barrier cuff forms a gap or pocket 500 that spaces the inner surface 502 of the cuff from the opening edge of the fabric to buffer or cushion the esophagus or other cord-like structure from the fabric edge.

In some circumstances, it may be desirable to provide an erosion resistant edge that is configured with a minimal gap, if any, between the barrier material and the fabric edge. In the illustrative embodiment shown in FIG. 7, the extensions 700, 702 of the margin barrier 116 and the surface barrier 118 are further secured to each other with an additional stitch line 49 located proximate to the fabric edge 54. This additional attachment essentially collapses the cavity 500 of the prior embodiments such that the erosion resistant barrier 114 is formed by the extensions 700, 702 of the margin barrier 116 and the surface barrier 118. With the cushion space eliminated, the erosion resistant barrier 114 acts to cushion the esophagus from the fabric edge by deflecting or bending about the fabric edge in a manner similar to that illustrated in FIG. 4, thereby engaging the esophagus with a relatively broad surface area that distributes potential erosion forces over a larger portion of the esophagus as compared to a thin edge. In the illustrative embodiment, the extensions 700, 702 of the barrier 114 have a length, or extension beyond the edge 54 of the layer of fabric 22, that is greater than the thickness t of the barrier material itself.

Although several embodiments of erosion resistant edges have been described, it is to be understood that the prosthesis may employ one or more erosion resistant edges of any suitable configuration as would be apparent to one of skill in the art. Additionally, while specific adhesion resistant barrier structures have been described above in connection with various portions of the prosthesis, it is to be appreciated that other suitable barrier structures may be employed with the prosthesis as would be apparent to one of skill in the art. For example, any one or combination of erosion resistant and/or adhesion resistant barriers may be formed by altering or treating the fabric so as to occlude tissue ingrowth, by covering the fabric with a barrier material, or any combination of fabric treatment and barrier materials. Additionally, any one or more of the barrier structures may be formed by both treating the fabric layer and covering the treated fabric with a barrier layer.

The prosthesis 20 may be provided with one or more erosion resistant and/or adhesion resistant barriers that are pre-attached to the fabric and/or other barriers. Alternatively, the prosthesis may be provided as a kit of separate parts with the barriers either being attached to the fabric and/or other barriers during the repair procedure or simply overlaid on a desired portion of the fabric 22 to be held in place by adjacent tissue and/or organs.

In one embodiment, the tissue infiltratable layer 22 is formed of a sheet of biologically compatible, flexible, prosthetic repair fabric having a plurality of interstices or openings which allow tissue ingrowth, integrating the repair device to host tissue after implantation. The suture pull-out strength of the tissue infiltratable layer and/or the barrier portions should be sufficient to support the underlying anatomical weakness and withstand the dynamic environment of the implant area. In the case of hiatal hernia repair, the mesh preferably has a suture pull-out strength of approximately 2 pounds per square inch and is sufficiently flexible to accommodate the dynamic environment about the esophagus during respiration, coughing, and swallowing. A representative material is knitted polypropylene monofilament mesh, such as BARD MESH, available from C. R. Bard, Inc. When implanted, the polypropylene mesh promotes rapid tissue ingrowth into and around the mesh structure. Alternatively, other surgical materials which are suitable for tissue reinforcement in defect closure may be utilized including, without limitation, polytetrafluoroethylene (PTFE) mesh, PROLENE, SOFT TISSUE PATCH (microporous ePTFE), SURGIPRO, TRELEX, ATRIUM, MERSELENE, non-absorbable collagen, and polyester. Absorbable materials, including polyglactin (VICRYL), polyglycolic acid (DEXON), and absorbable collagen may also be employed. It is contemplated that the fabric may be formed from monofilament or multifilament yarns which may be woven, knitted, molded, or otherwise interengaged to form the tissue infiltratable component of the implant.

In one embodiment, one or more of the barriers may be formed from a sheet of expanded polytetrafluoroethylene (ePTFE), such as GORE-TEX available from W. L. Gore & Associates, Inc., having a pore size (submicronal) that discourages tissue ingrowth and adhesion. A representative and non-limiting sampling of other suitable barrier materials includes silicone elastomer, such as SILASTIC Rx Medical Grade Sheeting (Platinum Cured) distributed by Dow Corning Corporation, TEFLON mesh, microporous polyproplyene sheeting (CELGARD), collagen, hyaluronic acid, carboxymethyl cellulose, and glycolic acid polymers. Autogenous, heterogeneous, and xenogenic tissue also are contemplated including, for example, pericardium and small intestine submucosa. Absorbable materials, such as oxidized, regenerated cellulose (INTERCEED (TC7)) may be employed for some applications. The barrier can be a blend, mixture, or hydrogel of any of the materials to form a temporary or permanent barrier for adhesion formation.

As indicated above, one or more of the barriers may be formed by treating or altering a portion of the tissue infiltratable layer to form a surface that does not promote tissue ingrowth. In one embodiment, one or more portions of the fabric layer are melted and resolidifed to render those portions of the fabric adhesion resistant. Other suitable techniques may include ultrasonic, induction, vibration, infrared/laser welding and the like. The fabric pores may be sealed with compatible materials to prohibit tissue ingrowth. It is to be appreciated that any suitable method may be used to reduce selected portions of the prosthesis adhesion resistant as would be apparent to one of skill in the art.

The prosthesis 20 of tissue infiltratable fabric and barrier regions is relatively flat and sufficiently pliable to allow a surgeon to manipulate the shape of the implant to conform to the anatomical site of interest and to be sutured or stapled thereto. Preferably, the prosthesis 20 is deliverable to the patient's cavity through a trocar or a laparoscopic cannula for skin incision. The shape and size of the prosthesis 20, including the fabric 22 and any of the barriers, may vary according to the surgical application as would be apparent to one of skill in the art. In this regard, it is contemplated that the fabric and/or any barrier may be preshaped or shaped by the surgeon during the surgical procedure.

In some instances, it may be desirable to pre-shape the prosthesis 20 to fit the general anatomy near a hiatal hernia. The prosthesis 20 may be shaped to fit within the abdominal cavity and be positioned under the diaphragm and around the esophagus or under the diaphragm and proximate the esophagus. Alternatively, the prosthesis may be shaped to fit within the thoracic cavity and positioned over the diaphragm, over any hiatus, and/or over any suture site for a cruroplasty or fundoplication. In the illustrative embodiment shown in FIGS. 1–2, the prosthesis has a curved shape suitable for augmenting or repairing a hiatal or other diaphragmatic hernia.

In the embodiment shown in FIG. 1, the prosthesis 20 includes a body portion 134 with a partial annular shape. The body portion includes an outwardly curving bottom edge 136, an inwardly curving opening edge 54 and a pair of side edges 138 that are angled so as to converge toward each other from the bottom edge toward the top edge. The top edge 54 forms a partial opening that is configured to receive and conform to the wall of the esophagus.

In an exemplary embodiment shown in FIGS. 1–2, the composite prosthesis 20 includes an approximately 0.025 to 0.030 inch thick sheet of BARD MESH knitted from polypropylene monofilament with a diameter of approximately 0.006 inches. The opening in the mesh fabric 22 has a radius of approximately 1.9 cm and a perimeter length of approximately 4.5 cm. The margin barrier 116 and the surface barrier 118 overlie the mesh fabric 22 proximate the fabric opening and each has an inner radius of curvature of approximately 1.4 cm and the margin barrier has an outer radius of curvature of approximately 2.4 cm. Accordingly, the margin barrier 116 has a width of approximately 1.0 cm of which approximately 0.5 cm overlays the margin surrounding the opening, and approximately 0.5 cm extends beyond the inner edge 54 of the mesh fabric 22 forming the extensions 700, 702. Alternative embodiments may extend the surfaces 700, 702 up to approximately 1.5 cm from the edge 54 of the opening in the fabric.

The outer edge and margin barriers 120, 122 are situated along the edges and margins of the outer periphery 32 of the mesh fabric 22 and formed by heat melding the mesh fabric 22 to close the interstices or openings in the mesh fabric 22. The outer margin barrier 122 has a width of approximately 1/16 to 3/8 inch. It should be understood, however, that these dimensions are merely exemplary and that any suitable sizes and shapes may be employed for the prosthesis 20.

Rather than providing the prosthesis with a separate erosion resistant barrier that is attached to the edge of the repair fabric, it may be desirable to configure the prosthetic repair fabric itself to include an integral erosion resistant edge that is adapted to engage with adjacent tissue and organs. In one illustrative embodiment shown in FIGS. 8–11, the prosthesis 21 includes a body of biocompatible repair fabric that may be provided in any desired shape for a particular application. The body includes first and second surfaces 26, 29 with a body edge 24 extending from the first surface 26 to the second surface 29. The first surface is adapted to face the defect and the second surface is adapted to face away from the defect. The body edge 24 is configured to inhibit erosion of adjacent tissue or organs due to contact with the prosthesis.

Figure 10:
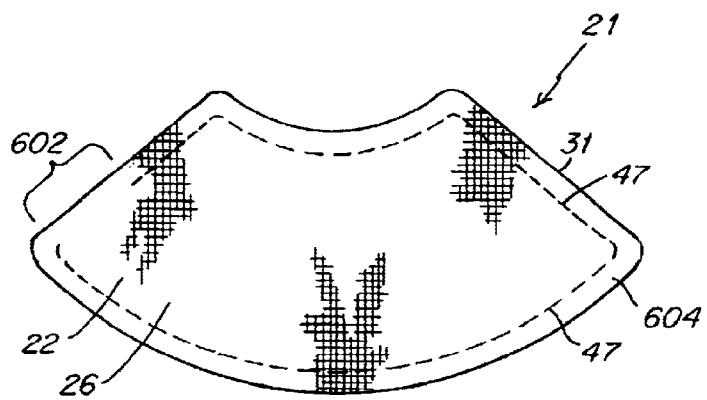
FIG. 10 is a top plan view of a prosthetic repair fabric of FIG. 8 illustrating layers of the prosthesis assembled to each other before inversion of the implant.
Figure 11:
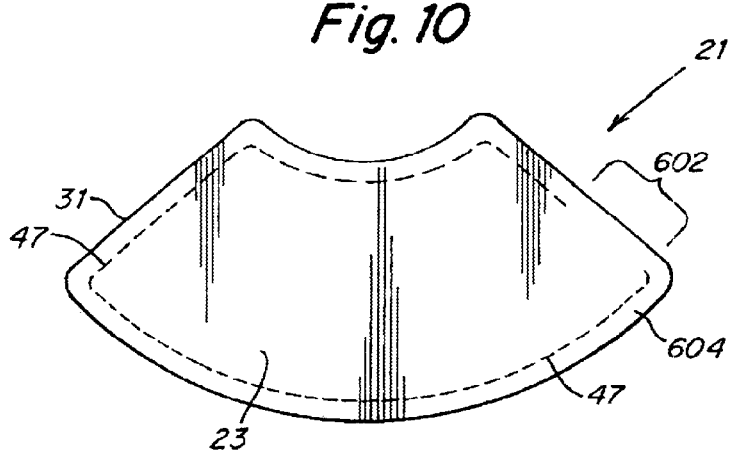
FIG. 11 is a bottom plan view of the assembled layers of the prosthetic repair fabric of FIG. 10.

In the illustrative embodiment, the body of repair fabric includes first and second layers of material that are attached to each other in a manner to form an erosion resistant edge. As shown in FIGS. 10–11, the first layer 22 is placed over and attached to the second layer 23 along at least one seam 47 with the second surface 29 of the second layer 23 initially facing the first surface 26 of the first layer 22. The layers 22, 23 may be attached proximate the outer periphery 31 of each layer using any suitable method apparent to one of skill in the art. In one embodiment, the layers are stitched to each other along a seam 47 located inward of the peripheral edges of the layers to create an extension or seam allowance 604 at the outer periphery of the implant 21.

Once attached to each other, the layers are inverted, or pulled right-side-out, such that the first surface 26 of the first layer 22 and the second surface 29 of the second layer 23 face outwardly away from each other. The second surface 28 of the first layer 22 then faces the first surface of the second layer 23 with a cavity 606 formed therebetween.

Inverting the fabric layers 22, 23 in this manner is facilitated with a pull-through opening 600 created by maintaining a gap 602 in the seam 47 at the outer periphery of the layer of fabric. In one embodiment, the gap is 1.5 to 2 inches in length for a prosthesis having a width of approximately 10 cm. However, those skilled in the art will recognize that other gap lengths may be appropriate for different sizes of the prosthetic repair fabric, different attachment methods, different fabric flexibilities, and different placement of the gap along the outer periphery 31 of the layer of fabric. In another embodiment, the gap 602 may be provided in the fabric itself, such as a slit formed in one of the fabric layers 22, 23. It is to be understood that any suitable arrangement may be implemented to facilitate forming a prosthesis in this manner.

Figure 9:
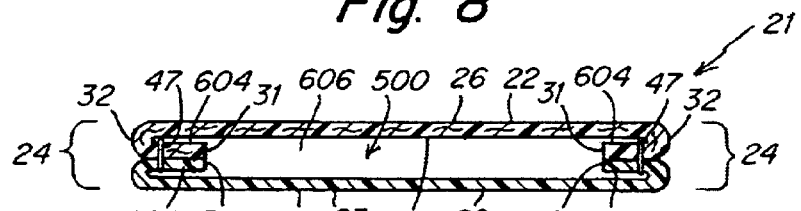
FIG. 9 is a cross-sectional view of the prosthetic repair fabric of FIG. 8 taken along section line 9—9.

As shown in FIG. 9, once the implant is inverted right-side-out, the seam allowance and peripheral edges of each layer are located inside the cavity 606 of the prosthesis, sandwiched between the two fabric layers 22, 23. In this manner, the seam 47 and fabric edges are isolated from the adjacent tissue and organs. The outer periphery 32 of the prosthetic repair fabric 21 is configured with a flat seam edge 24 that provides a relatively broad surface area to face adjacent tissue or organs for enhanced erosion resistance. The gap may be sealed, if desired, with attachment methods, such as stitching, after inversion of the prosthesis.

In the illustrative embodiment, erosion resistance of the prosthesis is further enhanced by the cavity space 606 internal to the prosthesis 21, which acts to bumper or pillow the esophagus, similar to the cushion space 500 discussed above. Moreover, folding the fabric layers around the internal seam allowance may increase the resilience or spring-like action of the prosthesis materials at the edge 24 to create a bumper or pillowing effect for adjacent tissue or organs which may contact the erosion resistant edge after the prosthesis 21 is implanted in the patient.

Figure 12:
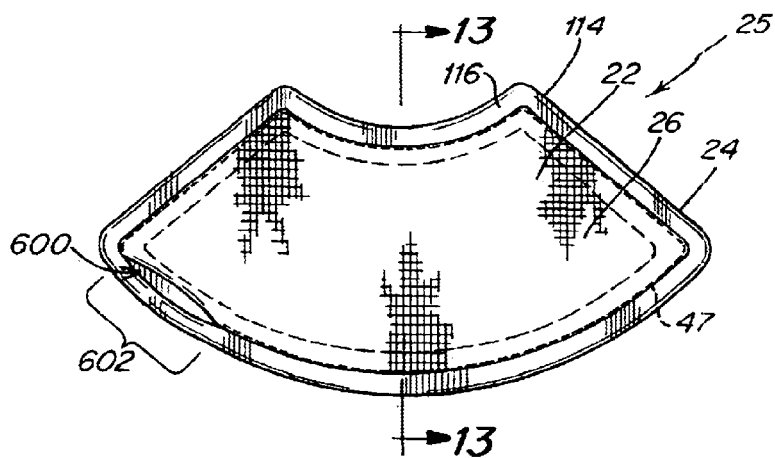
FIG. 12 is a top plan view of a prosthetic repair fabric in accordance with a further illustrative embodiment of the present invention.
Figure 13:
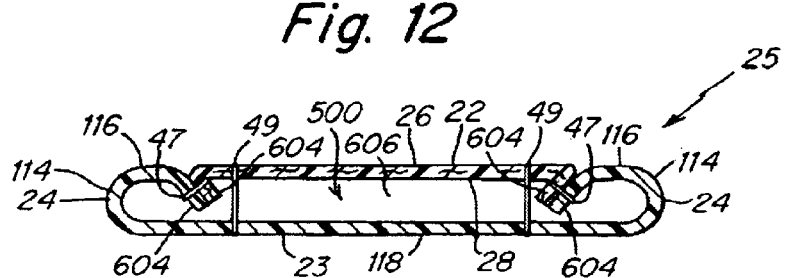
FIG. 13 is a cross-sectional view of the prosthetic repair fabric of FIG. 12 taken along line 13—13.

In the above-described embodiment, the fabric layers 22, 23 are substantially symmetric, such that each layer forms a substantially equal portion of the surface area of the edge 24 of the prosthesis 21. In some instances, it may be desirable to configure the prosthesis with one of the fabric layers forming the erosion resistant edge 24. In one illustrative embodiment as shown in FIGS. 12–13, the second layer 23 is configured to provide a proportionately larger surface area than, but a similar shape as, the first layer 22. With the seam allowances of the layers being substantially equal, the prosthesis 25, when flipped right-side-out as shown, will then have the flat seam connecting the fabric layers 22, 23 that is shifted in from the outer periphery 32 and located proximate the outer margin of the first surface of the prosthetic repair fabric. In this manner, the second layer 23 forms the erosion resistant edge 24 of the prosthesis.

To maintain placement of the flat seams at the margin of the first surface of the prosthesis, the second layer 23 may be attached to the first layer 22 after inversion of the prosthesis. As shown in the illustrative embodiment, a line of stitching 49 may attach the first layer 22 directly to the second layer 23 just inside the flat seam. The peripheral stitching maintains the centered placement of the first layer 22 over the second layer 23 to maintain the roll over of the fabric 23 at the outer periphery 32 of the prosthesis. It is to be understood that other attachment methods apparent to one of skill in the art may be employed to maintain the relative positioning of the layers. For example, intermittent stitches may be used throughout the body of the implant, or a line of continuous stitches may be located just outside the flat seam. In addition, the attachment method after inversion of the fabric may be located proximate the periphery 32 of the prosthesis such that the stitches attach the second layer 23 to itself without an intervening fabric layer 22.

In the illustrative embodiment, the first layer 22 includes a layer of tissue infiltratable fabric and the second layer 23 includes a barrier material that is resistant to adhesions with surrounding tissue and organs. In this regard, the second layer 23 forms a surface barrier 118 for preventing adhesions between the cavity viscera and the second surface of the fabric layer 22. In addition, the outer periphery 32 is then formed from the barrier material 118 folded over itself at the outer edge 32 of the prosthesis 25 to create an edge barrier 114 that is not only erosion resistant, but also adhesion resistant.

Figure 14:
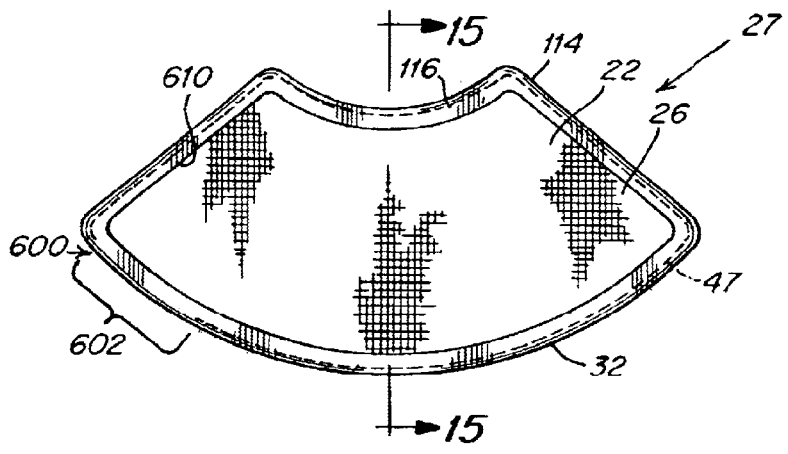
FIG. 14 is a top plan view of a prosthetic repair fabric in accordance with another illustrative embodiment of the present invention.
Figure 15:
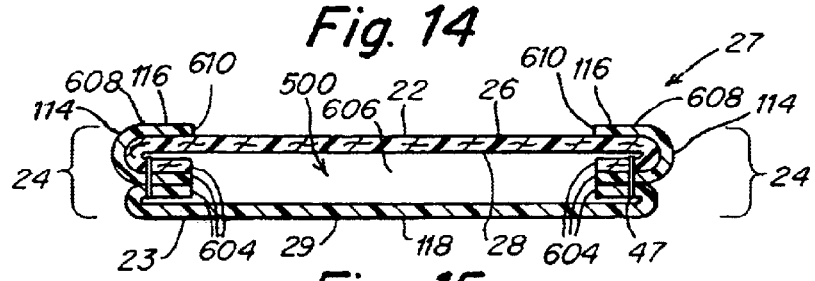
FIG. 15 is a cross-sectional view of the prosthetic repair fabric of FIG. 14 taken along line 15—15.
Figure 16:
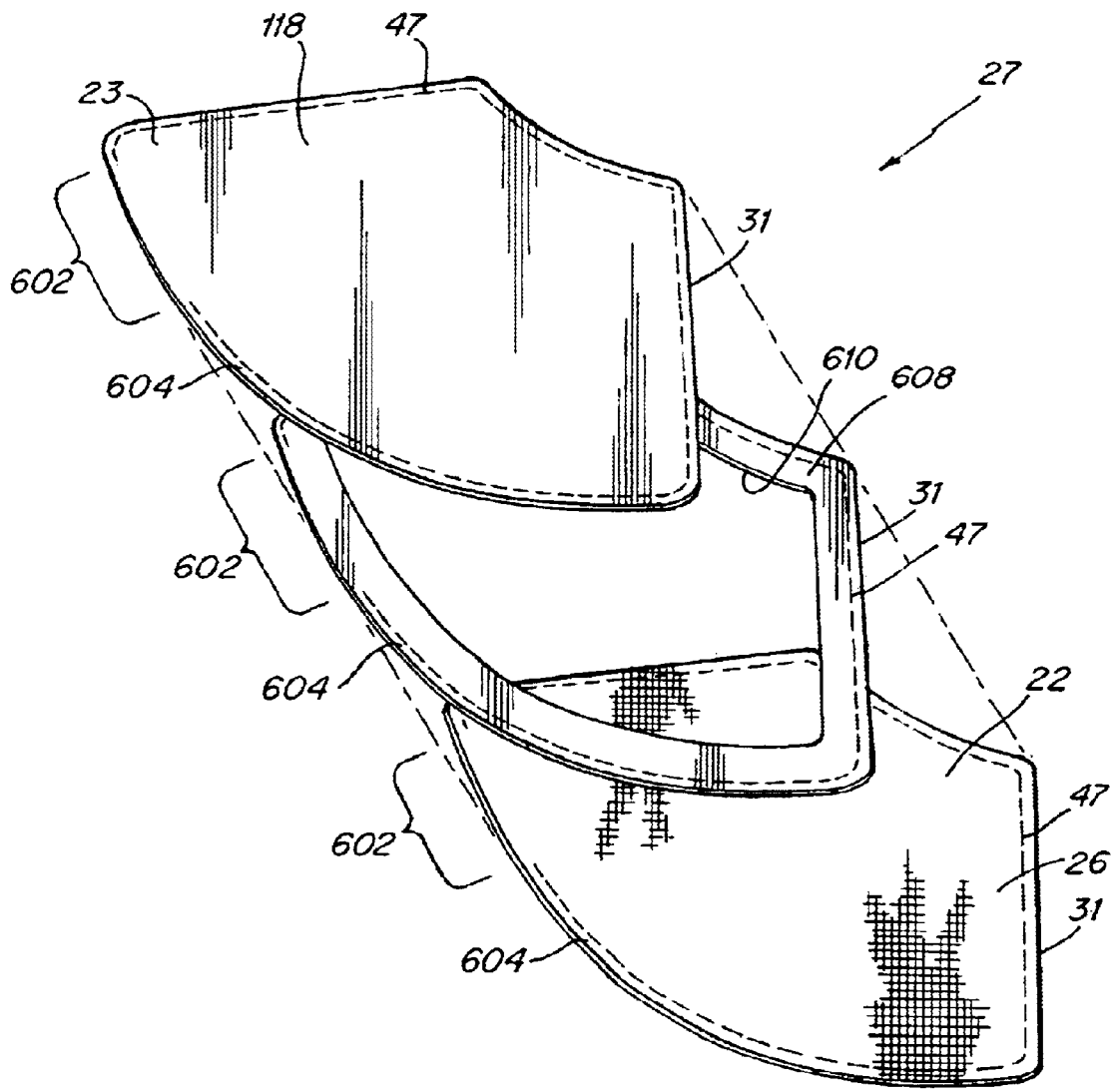
FIG. 16 is an exploded bottom perspective view of the prosthetic repair fabric of FIG. 14 before inversion of the implant.

In another illustrative embodiment as shown in FIGS. 14–16, a prosthesis 27 includes first and second layers 22, 23 of repair fabric configured in a manner similar to the prosthesis discussed above with reference to FIGS. 8–11. In this illustrative embodiment, the first layer 22 of fabric includes a layer of tissue infiltratable fabric and the second layer 23 of fabric includes a barrier material that is resistant to adhesions with tissue and organs to form a surface barrier 118. To ensure that the erosion resistant edge 24 is also adhesion resistant, the prosthesis also includes an edge barrier 114 that is arranged to cover at least a portion of the outer edge of the tissue infiltratable layer 22.

As shown in FIG. 16, the edge barrier 114 is formed with a barrier ring 608 that is sandwiched between the first surface 26 of the fabric layer 22 and the second surface of the barrier layer 118. The ring 608 is formed from a material that is resistant to adhesions with tissue and organs and its outer periphery is substantially symmetric to the outer periphery 31 of the fabric layer 22 and the barrier layer 118.

Once stacked, the fabric 22, barrier ring 608, and the barrier 118 are attached to each other proximate the periphery 31, as discussed above, while maintaining a pull-through opening 600 formed by a gap 602 in the seam. When the prosthesis 27 is inverted right-side-out, the outer periphery 32 is formed by a flat seam with the seam allowance 604 located within the cavity 606.

After inversion of the prosthesis as shown in FIG. 15, the barrier ring 608 creates an adhesion resistant edge barrier which lies against the first surface 26 of the layer of fabric 22 at the outer margin. The surface barrier 118 is disposed against the second surface 28 of the layer of fabric. In this regard, the outer periphery 32 of the prosthesis 27 is rendered adhesion resistant with the surface barrier 118 and the edge barrier 608 at the flat seam.

As is to be appreciated, the outer edge 32 of the prosthesis is also rendered erosion resistant since the seam allowances of each layer are enclosed within the cavity 606 and the peripheral edge 24 provides a broader surface area and a resilient bumper edge. Accordingly, the barrier ring 608 and the surface barrier 118, when pulled right-side out, create a smooth, roll over of barrier material at the peripheral edge 32 forming the edge barrier 114, the margin barrier 116, the outer edge barrier 120 and/or the outer barrier margin 122, as discussed above.

As shown in FIG. 14, the barrier ring 608 is configured to extend about the entire periphery of the fabric layer 22. In some circumstances, however, it may be desirable to limit the adhesion resistant edge to selected portions of the prosthesis. For example, the ring barrier 608 may be configured as a partial ring, which may be attached to the fabric and barrier layers, as discussed above. After inversion of the prosthesis, the partial ring 608 forms an edge barrier 114 about only a portion of the periphery of the prosthesis 20.

It may be desirable to configure the ring barrier 608 so as to reduce potential pockets of trapped visceral fluid. For example, the prosthesis 20 may be implanted in a position and orientation in which the prosthesis does not lie in a horizontal plane, such that fluid may potentially become trapped between the ring barrier 608 and the layer of fabric 22. In this manner, the ring barrier may be configured with its inner peripheral edge 610 facing downward to allow gravity to assist in draining trapped fluid.

As shown in the illustrative embodiment of FIGS. 14–16, the inner peripheral edge 610 of the barrier ring 608 remains unattached and lies against the first surface of the fabric 22. The barrier ring 608 is stretched across the edge and over a portion of the first surface of the layer of fabric 22. This arrangement creates some tension in the barrier ring 608 that maintains the ring in place around the outer margin of the peripheral edge 32. In this regard, the inner edge 610 of the ring barrier 608 remains unattached to the fabric and allows fluid flow between the barrier 608 and the fabric layer 22 to reduce the incidence of potential pockets of trapped visceral fluids.

Alternatively, the inner peripheral edge 610 may be pre-attached to the layer of fabric 22 before the outer peripheral stitching attaches the barrier ring, the fabric, and the surface barrier, or the inner peripheral edge 610 may be attached to the fabric layer after the prosthesis 27 is inverted inside-out with methods known in the art including, but not limited to, stitching, melding, and adhesives. Attachment of the inner circumference of the ring 608 may also attach the second layer 23 to the first layer 22 to maintain minimal spacing or control draping of the second layer 23.

After inversion of the prosthesis, the first and second layers 22, 23 may be further attached in the right-side-out configuration at the margin of the periphery 32 or throughout selected regions of the body of the prosthesis to maintain particular relative spacing and locations of the layer materials. For example, as discussed above, the fabric layer 22 may be attached to the surface barrier 118 around the margin of the periphery or throughout the body with intermittent or continuous stitches.

In one illustrative embodiment, the implant 27 of FIGS. 14–16 includes a fabric layer 22 formed of PTFE mesh, a barrier layer 118 formed of ePTFE, and an edge barrier 114 formed of ePTFE. It is to be appreciated that any suitable materials may be employed to form the prosthesis as would be apparent to one of skill in the art.

Figure 17:
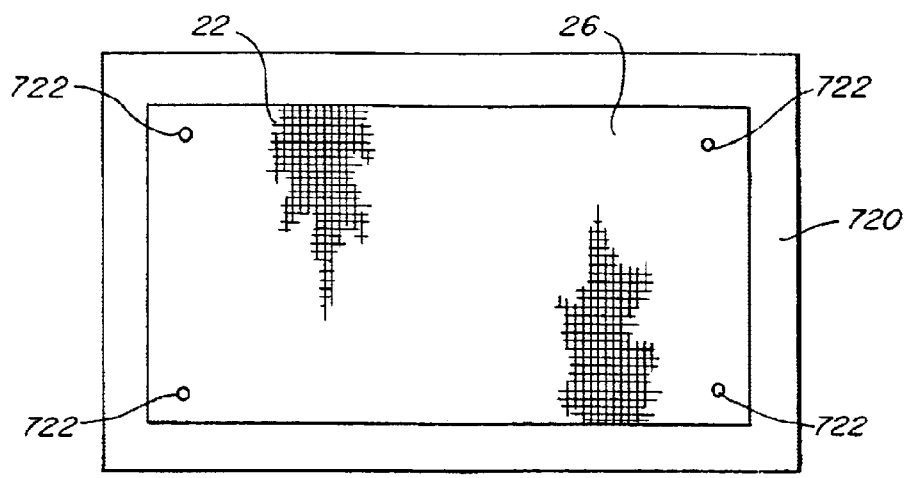
FIGS. 17–19 are schematic views of a manufacturing process for fabricating the prosthesis of FIGS. 14–16 in accordance with another illustrative embodiment of the present invention.
Figure 18:
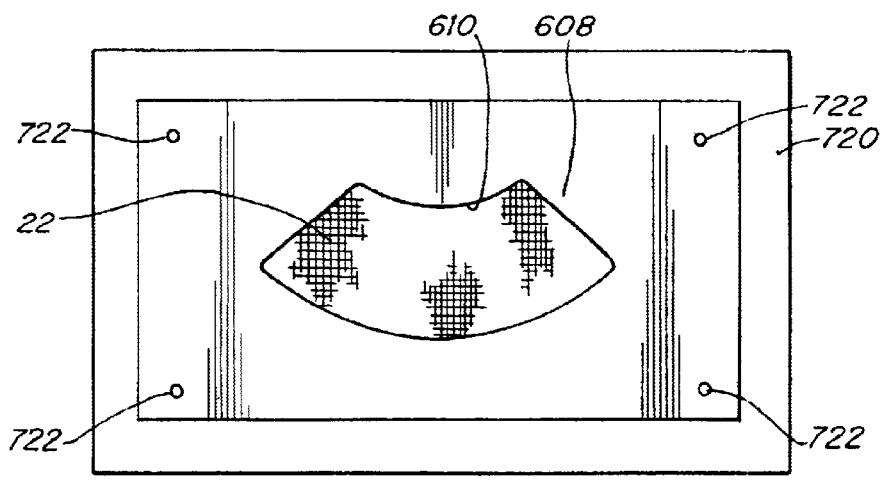
Figure 19:
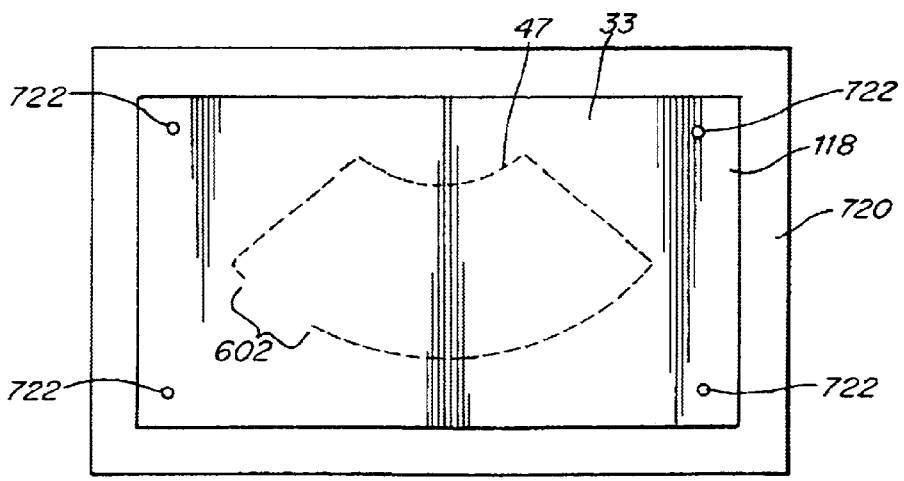

FIGS. 17–19 illustrate one embodiment of a manufacturing process for fabricating the prosthesis of FIGS. 14–16. As shown in FIG. 17, a rectangular sheet of PTFE mesh is clamped to a frame 720 with pins 722. The first surface 26 of the mesh fabric faces up from the frame. As shown in FIG. 18, a sheet 608 of ePTFE is then clamped in the frame over the mesh fabric 22. As shown, the sheet of ePTFE has a central region of barrier material removed to form the inner circumference 610 of the barrier ring 608. As shown in FIG. 19, a second sheet 118 of ePTFE is then clamped to the frame on top of the ePTFE barrier 608 with the first surface 33 of the barrier 118 facing up.

Once clamped in the frame 720, the layers are attached to each other with a stitch line 47 using approximately 4 mm to 6 mm long stitches formed of a polypropylene or PTFE monofilament. As illustrated in FIG. 19, the stitch line 47 follows the desired contour for the peripheral edge 32 of the prosthesis 27, leaving a gap 602 in the stitching having a length of approximately 1.5 inches. The stitch line 47 is placed approximately 5 mm outside the inner circumference 610 of the barrier 608. The prosthesis is then removed from the frame 720 by cutting the layers approximately 3 mm outside the stitch line 47, forming a seam allowance.

After removal from the frame, the ring barrier 608 forms an annular ring around the circumference of the prosthesis having a width of approximately 8 mm, of which 3 mm is outside the stitch line forming the seam allowance and approximately 5 mm overlies the first surface of the fabric layer forming the margin barrier 116. The prosthesis 20 is then inverted through the gap 602, placing the second side of the barrier layer 118, the first side of the layer of fabric, and the inner circumference of the ring barrier 608 external to the cavity 606, as shown in FIG. 15. The gap may then be stitched closed with stitches external to the cavity 606.

As described above, the various layers are aligned, stitched, cut, and then inverted. A template (not shown) may be provided indicating the placement of the various stitch lines and cut lines. For example, a template may outline the stitch line 47 and the placement of the gap 602. Additional template patterns may outline the placement of the cuts required to remove the prosthesis from the frame and the cut required to create the inner circumference of the ring barrier 608. Alternatively, the attachment or removal markings or indicia may be placed directly on the fabric or barrier layers. In one example, the first surface of the fabric layer 22 may indicate the proper placement of the inner circumference of the ring barrier 608, and the first surface of the surface layer 118 may indicate the outline of the stitches 47, the placement of the gap 602, and/or the outline of the cut line to create the seam allowance and remove the prosthesis from the frame. Those skilled in the art will recognize that many other methods may be employed to indicate the pattern or placement of the various layers, attachments, and cut lines.

The right-side-out prosthesis and method of isolating seam allowances within a prosthesis cavity may be particularly appropriate for attaching barrier materials and tissue infiltratable materials that have similar melting points. If the layers of material have similar melting temperatures, such as a fabric 22 formed from PTFE mesh and a barrier material formed from ePTFE, attaching the barrier material to the mesh fabric with heat sealing may no longer appropriate since both materials would melt away rather than fuse together. Similarly, if the melting temperature of the fabric layer 22 is greater than or equal to the melting temperature of the second layer 23, the interstices in the mesh fabric may not be heat sealed after construction of the implant to create an adhesion resistant barrier, since the heat seal would also melt any adjacent barrier material.

Figure 20:
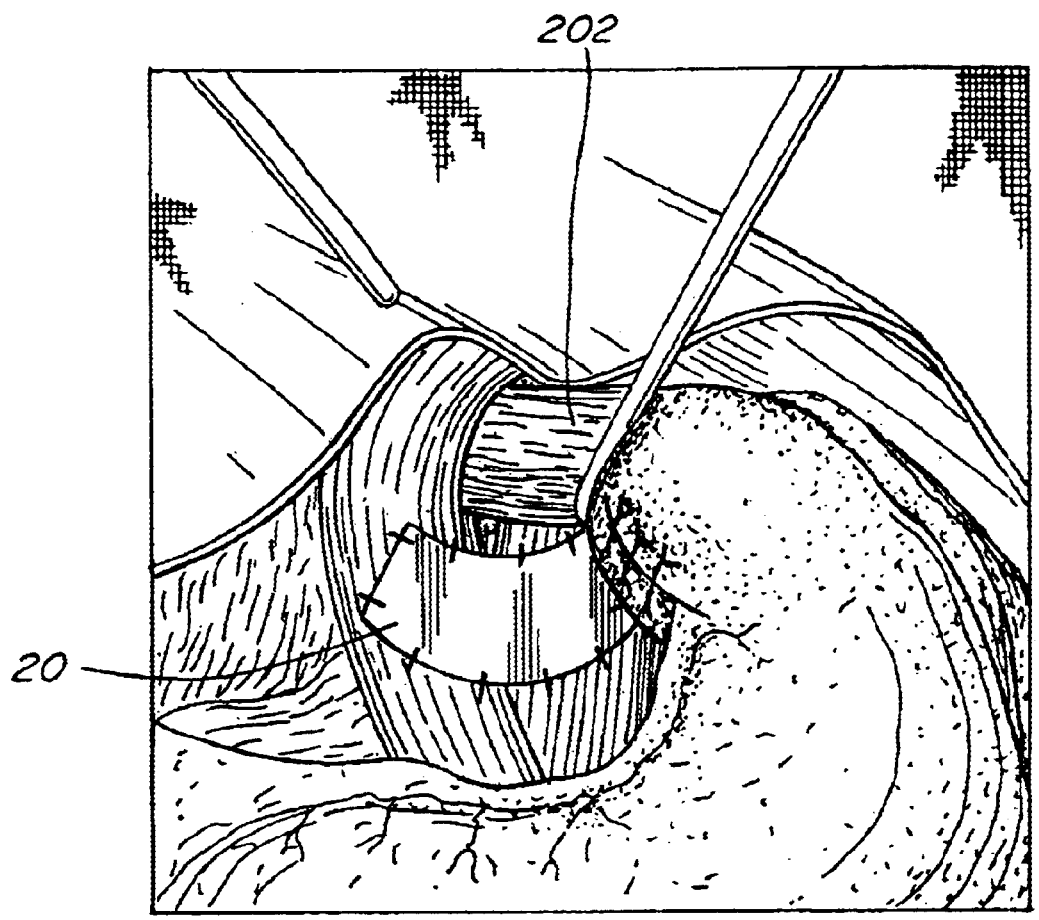
FIG. 20 is a schematic view illustrating the prosthetic repair fabric of FIG. 1 implanted in the abdominal cavity proximate to the esophagus.

FIG. 20 illustrates a representative application of the prosthesis in the repair of a hiatal hernia or in the treatment of GERD. The prosthesis 20 may be placed over the defect without approximating the tissue, effecting the repair in a substantially tension-free manner. Alternatively, the prosthesis may be employed in conjunction with a cruroplasty to reinforce the stitches with tissue infiltration over a surface area and alleviate the likelihood of suture pullout when a force is applied to the crura, that otherwise potentially could lead to recurrent herniation. It is to be understood that the prosthesis may be employed in any suitable manner for other procedures as would be apparent to one of skill.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A prosthetic repair fabric for repairing a tissue or muscle wall defect, the prosthetic repair fabric comprising:
   a body of implantable, biocompatible repair fabric, the body including first and second surfaces and a body edge that extends from the first surface to the second surface, the body including first and second layers joined to each other along an inverted seam that extends inwardly from the body edge and between the first and second layers to inhibit erosion of the tissue and organs.

2. The prosthetic repair fabric according to claim 1, wherein the first layer includes a layer of repair fabric that is susceptible to erosion into and the formation of adhesions with tissue and organs.

3. The prosthetic repair fabric according to claim 2, wherein the layer of fabric includes a plurality of interstices that are constructed and arranged to allow tissue ingrowth.

4. The prosthetic repair fabric according to claim 2, further comprising an edge barrier that inhibits the formation of adhesions with tissue and organs, the edge barrier being disposed about at least a portion of the body edge.

5. The prosthetic repair fabric according to claim 4, wherein the edge barrier extends over the portion of the body edge and over a portion of an outer surface of the first layer proximate the body edge.

6. The prosthetic repair fabric according to claim 4, wherein the edge barrier is joined to the first and second layers at the at least one seam.

7. The prosthetic repair fabric according to claim 4, wherein the edge barrier is formed from ePTFE.

8. The prosthetic repair fabric according to claim 4, wherein the body includes an opening that is adapted to receive a tube-like structure, the body edge including an opening edge that defines the opening in the body, and the edge barrier includes an opening edge barrier that extends about a portion of the opening edge to inhibit erosion into and the formation of adhesions with the tube-like structure.

9. The prosthetic repair fabric according to claim 2, wherein the first layer is formed from one of polypropylene mesh and PTFE mesh.

10. The prosthetic repair fabric according to claim 1, wherein the second layer includes a barrier material that inhibits the formation of adhesions with tissue and organs.

11. The prosthetic repair fabric according to claim 10, wherein the second layer is formed from ePTFE.

12. The prosthetic repair fabric according to claim 1, wherein the first layer is joined to the second layer by a series of stitches along the at least one seam.

13. The prosthetic repair fabric according to claim 1, wherein the first layer is symmetric to the second layer.

14. The prosthetic repair fabric according to claim 1, wherein the body includes an opening that is adapted to receive a tube-like structure, the body edge including an opening edge that defines the opening in the body.

15. The prosthetic repair fabric according to claim 14, wherein the prosthetic repair fabric is constructed and arranged to be placed proximate an esophageal hiatus, the opening being adapted to receive the esophagus.

16. The prosthetic repair fabric according to claim 1, wherein the first and second layers are formed of materials having substantially equal melting temperatures.

17. The prosthetic repair fabric according to claim 1, wherein the first layer is joined to the second layer inwardly from the body edge to reduce billowing of second layer.

18. A prosthetic repair fabric for repairing a tissue or muscle wall defect, the prosthetic repair fabric comprising:
   a body of implantable, biocompatible repair fabric, the body including first and second surfaces and a body edge extending from the first surface to the second surface, the first surface adapted to face the muscle or tissue wall defect and the second surface adapted to face away from the defect, the body including first and second layers, each of the first and second layers having an outer surface and an inner surface, the outer surface of the first layer forming a portion of the first surface of the body and the outer surface of the second layer forming the second surface of the body with the inner surface of the first layer facing the inner surface of the second layer, the first and second layers being joined to each other along at least one seam, the at least one seam being disposed inwardly of the body edge between the inner surfaces of the first and second layers to inhibit erosion of the tissue and organs by the body edge.

19. The prosthetic repair fabric according to claim 18, wherein the first layer includes a layer of repair fabric that is susceptible to erosion into and the formation of adhesions with tissue and organs.

20. The prosthetic repair fabric according to claim 19, wherein the layer of fabric includes a plurality of interstices that are constructed and arranged to allow tissue ingrowth.

21. The prosthetic repair fabric according to claim 19, further comprising an edge barrier that inhibits the formation of adhesions with tissue and organs, the edge barrier being disposed about at least a portion of the body edge.

22. The prosthetic repair fabric according to claim 21, wherein the edge barrier extends over the portion of the body edge and over a portion of the outer surface of the first layer proximate the portion of the body edge.

23. The prosthetic repair fabric according to claim 21, wherein the edge barrier is joined to the first and second layers at the at least one seam.

24. The prosthetic repair fabric according to claim 21, wherein the edge barrier is formed from ePTFE.

25. The prosthetic repair fabric according to claim 21, wherein the body includes an opening that is adapted to receive a tube-like structure, the body edge including an opening edge that defines the opening in the body, and the edge barrier includes an opening edge barrier that extends about a portion of the opening edge to inhibit erosion into and the formation of adhesions with the tube-like structure.

26. The prosthetic repair fabric according to claim 19, wherein the first layer is formed from one of polypropylene mesh and PTFE mesh.

27. The prosthetic repair fabric according to claim 18, wherein the second layer includes a barrier material that inhibits the formation of adhesions with tissue and organs.

28. The prosthetic repair fabric according to claim 27, wherein the second layer is formed from ePTFE.

29. The prosthetic repair fabric according to claim 18, wherein the first layer is joined to the second layer by a series of stitches along the at least one seam.

30. The prosthetic repair fabric according to claim 18, wherein the first layer is symmetric to the second layer.

31. The prosthetic repair fabric according to claim 18, wherein a shape of the first layer has the same shape as a shape of the second layer, wherein the shape of the second layer is proportionately larger than the shape of the first layer.

32. The prosthetic repair fabric according to claim 31, wherein the body edge is formed entirely by the second layer.

33. The prosthetic repair fabric according to claim 18, wherein the body includes an opening that is adapted to receive a tube-like structure, the body edge including an opening edge that defines the opening in the body.

34. The prosthetic repair fabric according to claim 33, wherein the prosthetic repair fabric is constructed and arranged to be placed proximate an esophageal hiatus, the opening being adapted to receive the esophagus.

35. The prosthetic repair fabric according to claim 18, wherein the first and second layers are formed of materials having substantially equal melting temperatures.

36. The prosthetic repair fabric according to claim 18, wherein a portion of the at least one seam is located on the first surface of the body.

37. The prosthetic repair fabric according to claim 36, wherein the body edge proximate to the portion of the at least one seam is formed entirely of the second layer.

38. The prosthetic repair fabric according to claim 18, wherein the body edge includes portions of the first layer and the second layer, the at least one seam extending inwardly from the body edge and between the first and second layers.

39. The prosthetic repair fabric according to claim 18, wherein the first layer is joined to the second layer inwardly from the body edge to reduce billowing of the second layer.

* * * * *